United States Patent [19]

Motobayashi

[11] 4,386,053
[45] May 31, 1983

[54] TEST PIECE FOR DETECTION OF OCCULT BLOOD

[75] Inventor: Hiroshi Motobayashi, Tokyo, Japan

[73] Assignee: Terumo Corporation, Tokyo, Japan

[21] Appl. No.: 297,823

[22] Filed: Aug. 31, 1981

[51] Int. Cl.³ ........................................... G01N 33/72
[52] U.S. Cl. ...................................... 422/56; 435/28; 436/66; 436/904
[58] Field of Search ..................... 23/230 B, 932, 931; 422/56; 252/408; 435/28; 436/66, 904

[56] References Cited

U.S. PATENT DOCUMENTS 4,290,773 9/1981 Magers et al. ................... 23/932 X

FOREIGN PATENT DOCUMENTS 53-143396 12/1978 Japan.

OTHER PUBLICATIONS

Derwent Abstract of Japanese Kokai.
Motobayashi–Chemical Abstract of Japanese Kokai, vol. 92, 1980, No. 92:37281t.

Primary Examiner—Arnold Turk
Attorney, Agent, or Firm—Frishauf, Holtz, Goodman & Woodward

[57] ABSTRACT

In a test piece for the detection of occult blood, obtained by impregnating a substrate with an organic peroxide, a chromogen, a buffer, and a stabilizer, at least one compound selected from the group of compounds represented by the general formula I:

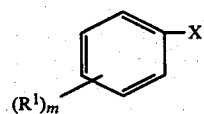

(I)

wherein, m denotes an integer of the value of 1 to 5, $R^1$ denotes one member selected from the group consisting of methyl group, lower alkoxy group, halogen atoms, and hydrogen atom, and X denotes one group selected from the group consisting of

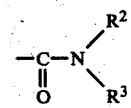

where, $R^2$ and $R^3$ each denote an alkyl group having 1 or 2 carbon atoms,

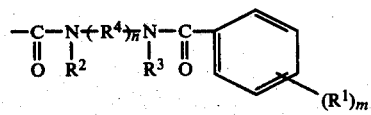

where, m, $R^1$, $R^2$, and $R^3$ are as defined above, $R^4$ denotes an alkylene group having 1 to 6 carbon atoms, and n is 0 or 1,

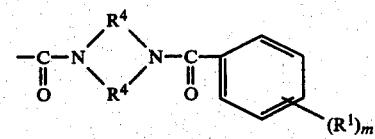

where, m, $R^1$, $R^4$ are as defined above, and

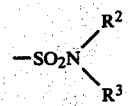

where, $R^2$ and $R^3$ are as defined above.

15 Claims, No Drawings

TEST PIECE FOR DETECTION OF OCCULT BLOOD

BACKGROUND OF THE INVENTION

1. Field of the Invention

This invention relates to a test piece for the detection of occult blood. More particularly, this invention relates to a stable test piece for easy detection of blood and other peroxidatively active substance in body fluid.

2. Description of Prior Arts

Presence of blood or peroxidatively active hemoglobin in body fluid such as, for urine, feces or vomit may be regarded as an indication of a certain disease such as inflammation ulcer or tumor in the stomach, the kidney, the intestines and other urinary organs. In this case, therefore, it is clinically very important that diagnosis or therapy should be given with minimum loss of time. For this purpose, it is necessary that the blood or peroxidatively active substance present in the body fluid should be detected accurately.

Virtually all the conventional methods adopted for the detection of occult blood in given body fluids have utilized the peroxidative activity of occult blood. For example, a test piece has been prepared by impregnating a carrier such as filter paper with an organic hydroperoxide and an organic color-forming indicator as a chromogen. When peroxidatively active blood or free hemoglobin comes into contact with this test piece, it decomposes the aforementioned hydroperoxide with liberation of oxygen and the produced oxygen oxidizes the organic color-forming indicator and causes it to assume a color.

The organic color-forming indicator contained in the test piece possesses an oxidative power and the organic hydroperoxide also contained in the test piece is a reactive substance and, therefore, is potentially incompatible with the indicator. Since these incompatible components coexist in the test piece, they are essentially readily reactive with each other. Thus, the test piece does not withstand prolonged preservation. With a view to inhibiting this unwanted reaction of the two components during the storage of the test piece, it has been proposed to incorporate in the test piece a stabilizer. Examples of stabilizers proposed to date include di- or trimorpholide phosphate type compounds (U.S. Pat. No. 3,853,471), amine salt of organic hydroperoxide (U.S. Pat. No. 4,017,261), and boric esters (U.S. Pat. No. 4,071,321). Among the conventional stabilizing methods is included a method which involves microcapsulating an organic hydroperoxide with a glutinous substance such as gelatin.

The conventional techniques adopted for the incorporation of stabilizers have invariably been aimed at stabilizing the potentially incompatible reagents (organic hydroperoxide and organic color-forming indicator) by preventing them from quickly mingling with each other. Di- or trimorpholide phosphate type compounds are primarily insectifuges (contraceptives for insects). Because of their violent actions, therefore, their manufacture is hazardous and their handling calls for the utmost care. Amine salts of organic hydroperoxides are highly volatile. Test pieces containing such compounds, therefore, readily affect other test papers placed nearby. In the case of boric esters, since they are used in combination with dimethyl sulfoxide, for example, the test pieces incorporating these compounds similarly affect other test papers placed nearby. Thus, the conventional stabilizers have their demerits. In the case of the microcapsulation of an organic hydroperoxide, there is entailed a disadvantage that the microcapsule, on aging, becomes sufficiently rigid as to jeopardize the readiness of the reaction and impair the uniformity of the reaction in the test piece, with the result that the color is formed unevenly. Since the conventional reagents and test pieces have been unstable as described above, it has occurred rather frequently that the colors developed by the test pieces defy accurate discernment.

An object of this invention, therefore, is to provide a novel test piece for the detection of occult blood in body fluids.

Another object of this invention is to provide a test piece for the detection of occult blood, which is possessed of improved color sensitivity for the sake of easy detection.

SUMMARY OF THE INVENTION

The object described above is accomplished by a test piece for the detection of occult blood, i.e. a peroxidatively active substance, in body fluids, obtained by impregnating a substrate with an organic hydroperoxide, a chromogen, a buffer, and a stabilizer, which test piece is characterized by the stabilizer being at least one compound of the general formula I:

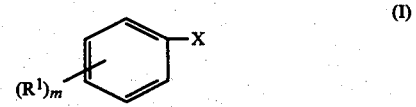

wherein, m denotes an integer of the value of 1 to 5, $R^1$ denotes one member selected from the group consisting of methyl group, lower alkoxy group, halogen atoms and hydrogen atom, and X denotes one member selected from the group consisting of

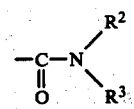

where, $R^2$ and $R^3$ each denote an alkyl group having 1 or 2 carbon atoms,

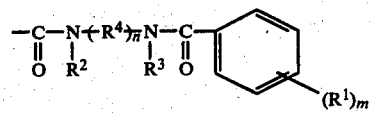

where, m, $R^1$, $R^2$ and $R^3$ are as defined above, $R^4$ denotes an alkylene group having 1 to 6 carbon atoms, and n denotes 0 or 1,

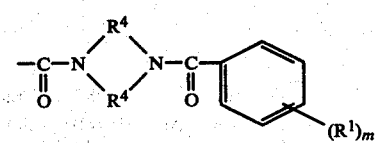

where m, $R^1$ and $R^4$ are as defined above, and

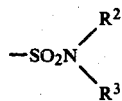

where, $R^2$ and $R^3$ are as defined above.

DETAILED DESCRIPTION OF THE INVENTION

The stabilizer which is used in the present invention is a compound of the aforementioned general formula I:

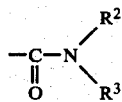
(I)

wherein, m denotes an integer of the value of 1 to 5, preferably of 1, $R^1$ denotes one member selected from the group consisting of methyl group, lower alkoxy group having 1 to 6 carbon atoms in the alkyl moiety, halogen atoms, and hydrogen atom, preferably methyl group, methoxy group, bromine atom, chlorine atom or hydrogen atom, X denotes one member selected from the group consisting of

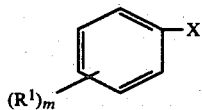

where, $R^2$ and $R^3$ each denote an alkyl group having 1 or 2 carbon atoms,

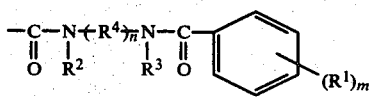

where, m, $R^1$, $R^2$, and $R^3$ are as defined above, $R^4$ denotes an alkylene group having 1 to 6, preferably 2 to 6, carbon atoms, and n denotes 0 or 1,

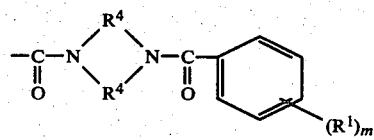

where, m, $R^1$ and $R^4$ are as defined above, and

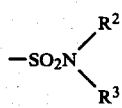

where, $R^2$ and $R^3$ are as defined above. This compound is soluble in water or alcohols. Desirably, it has a melting point of at least 45° C. to enjoy thermal resistance.

When X is

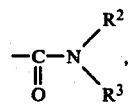

the compound of the general formula I is a compound represented by the general formula II.

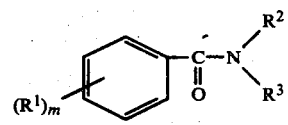
(II)

wherein, m, $R^1$, $R^2$ and $R^3$ are as defined above.

When X is

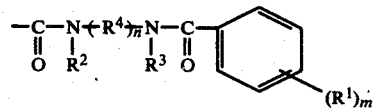

the compound of the general formula I is a compound represented by the general formula III.

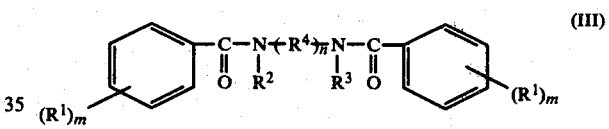
(III)

wherein, m, $R^1$, $R^2$, $R^3$, $R^4$ and n are as defined above.

When X is

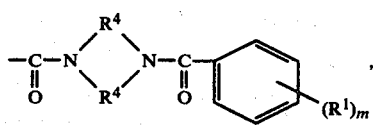

the compound of the general formula I is a compound represented by the general formula IV.

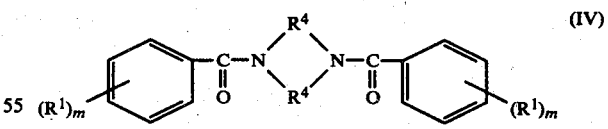
(IV)

wherein, M, $R^1$, and $R^4$ are as defined above.

When X is

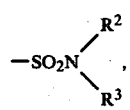

the compound of the general formula I is compound represented by the general formula V.

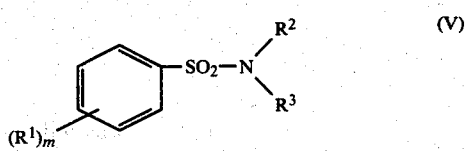

wherein, m, R[1], R[2], and R[3] are as defined above.

Typical compounds of the general formula I are p-bromobenzyl dimethylamide, p-chlorobenzoyl dimethylamide, benzoyl dimethylamide, anisoyl dimethylamide, p-bromobenzoyl diethylamide, p-chlorobenzoyl ethylamide, N,N'-dibenzyl-N,N'-dimethyl hydrazine, N,N'-dibenzyl-N,N'-diethyl hydrazine, N,N'-ditoluoyl-N,N'-dimethyl hydrazine, N,N'-ditoluoyl-N,N'-diethyl hydrazine, N,N'-dibromobenzoyl-N,N'-dimethyl hydrazine, N,N'-dichlorobenzoyl-N,N'-dimethyl hydrazine, N,N'-dibromobenzoyl-N,N'-diethyl hydrazine, N,N'-dianisoyl-N,N'-dimethyl hydrazine, N,N'-dianisoyl-N,N'-diethyl hydrazine, N,N'-dibenzoyl-N,N'-diethylethylene diamine, N,N'-dibenzoyl-N,N'-dimethylethylene diamine, N,N'-dibenzoyl-N,N'-diethylhexamethylene diamine, N,N'-dibenzoyl-N,N'-dimethylhexamethylene diamine, N,N'-dichlorobenzoyl-N,N'-diethylhexamethylene diamine, N,N'-dibromobenzoyl-N,N'-diethylhexamethylene diamine, N,N'-dianisoyl-N,N'-diethyl-hexamethylene diamine, N,N'-ditoluoyl-N,N'-diethylhexamethylene diamine, N,N'-dibenzoyl diethylene diamine, N,N'-dibromobenzoyl-N,N'-diethylene diamine, N,N'-ditoluoyl-N,N'-diethylene diamine, N,N-dianisoyl-N,N'-diethylene diamine, p-toluene sulfonyl-N-diethylamide, p-bromobenzene sulfonyl-N-dimethylamide, p-methoxybenzene sulfonyl-N-diethylamide, and N,N'-dimethylbenzene sulfonamide.

Now, the method for the manufacture of N,N'-dibenzoyl-N,N'-diethylethylene diamine which is one of the compounds usable as the stabilizer in the test piece of the present invention will be described below by way of illustration.

DESCRIPTION OF SYNTHESIS

A chloroform solution of benzoyl chloride is obtained by adding 11.5 ml of benzoyl chloride to 50 ml of chloroform. Separately, a chloroform solution of N,N'-diethylethylene diamine is obtained by adding 7.1 ml of N,N'-diethylethylene diamine to 50 ml of chloroform. The two solutions are gently mixed while under cooling. To this mixture, 25 ml of an aqueous 20 percent sodium carbonate solution is added. The resultant solution is heated at 60° C. for one hour. The reaction solution thus obtained is vacuum dried with an evaporator. For the removal of salt, the reaction product is again dissolved in chloroform and the resultant solution is dried with an evaporator. Consequently, there is obtained 14.2 g of N,N'-dibenzoyl-N,N'-diethylethylene diamine.

Examples of organic hydroperoxides which are advantageously usable for this invention include 2,5-dimethylhexane-2,5-dihydroperoxide, cumene hydroperoxide, 2,5-dimethylhexanone-2,5-dihydroperoxide, diisopropylbenzene hydroperoxide, 6-butyl hydroperoxide, p-methane hydroperoxide, and 4-methylphenyl isopropyl hydroperoxide. Among other organic hydroperoxides enumerated above, 2,5-dimethylhexanone-2,5-dihydroperoxide, cumene hydroperoxide, and 2,5-dimethylhexanone-2,5-dihydroperoxide are preferable because of their relatively low decomposition ratios.

The chromogens for the purpose of this invention are those which form colors on oxidation and which are called "oxidation indicators." Examples of such chromogens include orthotoluidine, benzidine, 3,3',5,5'-tetramethylbenzidine, 2,7-diaminofluorene, mixtures containing such compounds in varying proportions, guaiacols, various substituted phenylene diamines, pyridine derivatives, substituted azines, and leuco-malachite green.

When the test piece is immersed in the body fluid, the pH value thereof is required to be maintained in the range of from 4 to 8, preferably from 5 to 7. Thus, the buffer is used for the purpose of maintaining the pH value of the composition retained in the test piece. Examples of buffers which are advantageously usable for the invention include citric acid-sodium citrate, tartaric acid-sodium tartrate, malic acid-borax, hydrogen potassium phthalate-dipotassium phthalate, and hydrogen sodium succinate-disodium succinate.

With a view to ensuring uniform infusion of the body fluid in the test piece, it is desirable to incorporate a wetting agent in the composition for the test piece. Typical wetting agents are surface active agents including alkyl sulfates such as sodium lauryl-sulfate, sodium dodecyl-sulfate, and sodium tetradecyl-sulfate, alkylbenzene sulfonates such as sodium dodecylbenzene sulfonate, and dialkyl sulfosuccinates such as sodium dioctyl sulfo-succinate and sodium diheptyl sulfosuccinate.

Optionally, the test piece of the present invention may incorporate a reagent capable of enhancing the peroxidase activity of hemoglobin. Typical enhancers usable for this purpose are quinoline and derivatives thereof, including quinine, cinchonine, 6-methoxyquinoline, quinaldine, 8-amino-6-methoxy quinoline, 2-quinolinol, isoquinoline, benzo[f]quinoline, and 3-amino-quinoline. The presence of such an enhancer in the test piece generally serves to accelerate the reaction velocity of oxidation and heighten the sensitivity of the test piece itself.

A tackifier may be used for the purpose of preventing the composition from oozing out of the test piece. Typical tackifiers suitable for this purpose include polymers such as polyvinyl alcohol, polyvinyl pyrrolidone, polyethylene glycol, polyacrylates, polyacrylamide, poly(hydroxyethyl methacrylate), poly(hydroxyethyl acrylate), and carboxymethyl cellulose, and gelatin and gum arabic.

The amounts of the reagents to be used in the test piece of the present invention are 1 to 10,000 parts by weight, preferably 100 to 1,000 parts by weight, of the chromogen, 10 to 10,000 parts by weight, preferably 100 to 1,000 parts by weight, of the buffer, 10 to 10,000 parts by weight, preferably 100 to 1,000 parts by weight, of the stabilizer, 0 to 1,000 parts by weight, preferably 10 to 100 parts by weight, of the wetting agent, 0 to 10,000 parts by weight, preferably 100 to 1,000 parts by weight, of the peroxidase activity enhancer (sensitizer), and 0 to 10,000 parts by weight, preferably 100 to 1,000 parts by weight of the tackifier respectively based on 100 parts by weight of the organic hydroperoxide. The combined amount of these reagents to be carried is from 0 to 50 weight percent, preferably from 0 to 10 weight percent, based on the substrate.

These reagents are first dissolved in a suitable solvent such as benzene, toluene, methanol, ethanol, chloroform or water and the resultant solution is caused to impregnate the substrate. For example, an organic hydroperoxide and a stabilizer are dissolved in a solvent and the substrate is amply wetted in the resultant solution. The wet substrate is then dried. Then, a tackifier and a buffer are dissolved in a solvent. The aforementioned substrate is amply wetted in this solution and then dried. Finally, a chromogen and a peroxidase activity enhancer are dissolved in a solvent and the same substrate is amply wetted with the resultant solution and dried. Consequently, a test piece for the detection of occult blood is obtained.

As the substrate, there can be used filter paper, glass fiber, or non-woven faric made of plastic material. Any other substrate may be adopted on condition that the substrate does not react with the impregnants or does not dissolve therein and is absorptive.

The test piece of the present invention for the detection of occult blood is immersed in the body fluid for about one second, then removed from the body fluid, and allowed to stand in air for 60 seconds to be readied for the rating. The rating is carried out by comparing the color formed by the test piece with the standard color table, finding the matching color in the table, and noting the symbol indicated accordingly. The concentration of the occult blood in the body fluid can be determined based on the degree of color formation which is found from the standard color table as described above.

Now, the present invention will be described in detail below with reference to several working examples. It should be noted that the invention is not limited by these examples.

EXAMPLE 1

| Solution I | | |
|---|---|---|
| 2,5-Dimethylhexane-2,5-dihydroperoxide | 1.5 | g |
| Sodium dioctyl sulfo-succinate | 1.0 | g |
| p-Bromobenzoyl dimethylamine | 10 | g |
| Methanol | 100 | ml |

Solution I was prepared by mixing the compounds indicated above. A filter paper was thoroughly wetted in the solution I, then removed from the solution, and dried in an oven at 40° C. for 20 minutes.

| Solution II | | |
|---|---|---|
| Gelatin | 2.0 | g |
| Citric acid | 2.5 | g |
| Sodium citrate | 7.5 | g |
| Water | 100 | ml |

Solution II was prepared by mixing the compounds indicated above. The aforementioned filter paper which had been impregnated with the solution I and dried was thoroughly wetted with the solution II, removed from the solution and then dried in an oven at 40° C. for 50 minutes.

| Solution III | | |
|---|---|---|
| Ortho-toluidine | 0.3 | g |
| 3-Amino-quinoline | 0.3 | g |
| Benzene | 100 | ml |

Solution III was prepared by mixing the compounds shown above. The aforementioned filter paper which had been impregnated with the solution II and dried was thoroughly wetted with the solution III, removed from the solution, and dried in an oven at 50° C. for 10 minutes. Thus was obtained a test piece for the detection of occult blood.

EXAMPLE 2

The procedure of Example 1 was followed, except that N,N'-dibenzoyl-N,N'-dimethyl hydrazine was used as the stabilizer in the place of p-bromobenzoyl dimethylamide. Thus, a test piece for the detection of occult blood was produced.

EXAMPLE 3

The procedure of Example 1 was followed, except that N,N'-dibenzoyl-N,N'-diethylethylene diamine was used as the stabilizer in the place of p-bromobenzoyl dimethylamide.

EXAMPLE 4

The procedure of Example 1 was followed, except that p-toluene sulfonyl-N-diethylamine was used as the stabilizer in the place of p-bromobenzoyl dimethylamide.

EXAMPLE 5

The procedure of Example 1 was followed, except that N,N'-ditoluoyl-N,N'-diethylene diamine was used as the stabilizer in the place of p-bromobenzoyl dimethylamide.

EXAMPLE 6

To a mortar, 100 ml of gum arabic mucilage (prepared by adding 200 g of gum arabic to 500 ml of boiling water) and 2 ml of dioctyl sodium sulfo-succinate (5 percent w/v) were added in the order mentioned. Further, 5 ml of cumene hydroperoxide was added. The resultant mixture was ground in the mortar for five minutes to produce a crude emulsion. Separately, a citrate buffer was prepared by adding a mixture consisting of 163 g of sodium citrate and 37 g of citric acid to 1500 ml of boiling water. The citrate buffer was mixed with 0.7 g of gelatine. Then, 50 ml of the resultant buffer-gelatine mixture and the crude emulsion were thoroughly stirred. Subsequently, 1 ml of a 1-percent dispersion of dialdehyde starch was added while thoroughly stirring. Finally, 12 ml of an aqueous 5 percent sodium laurate solution was added to afford a composition. This composition was homogenized in a manual homogenizer. While under stirring, 50 ml of the buffer which had been prepared by using 500 ml of water, 163 g of sodium citrate, and 37 g of citric acid as described above was added to the homogenized composition. In the resultant emulsion, a slender piece of paper was immersed to be impregnated. The wet piece of paper was dried in an oven at 75° to 80° C. for 24 hours. Finally, a solution of 320 mg of ortho-toluidine in 16 ml of chloroform was applied to the slender piece of paper by immersion. The wet paper was gently heated to expel excess chloroform. Consequently, there was obtained a test piece for the detection of occult blood.

EXAMPLE 7

The test pieces for the detection of occult blood obtained in Examples 1-6 were allowed to stand at 37° C. and kept under observation for change of appearance by aging. The results were as shown in Table 1. These results permit evaluation of the test pieces with respect to stability to withstand degradation by aging.

TABLE 1

| Test piece | Change of appearance by aging | | | |
|---|---|---|---|---|
| | One week | Two weeks | Three weeks | Four weeks |
| Example 1 | No change | No change | No change | Slight change to brown |
| Example 2 | " | " | " | No change |
| Example 3 | " | " | " | " |
| Example 4 | " | " | " | Slight change to brown |
| Example 5 | " | " | " | No change |
| Example 6 | " | Change to black | Change to black | Change to black |

It is seen from Table 1 that the test pieces of Examples 1-5 conforming to the present invention showed absolutely no change during three weeks' standing. In contrast, the test piece of Example 6 conforming to the conventional method changed to black after only two weeks' standing. This fact demonstrates that the test pieces of Examples 1-5 according to the present invention excelled in stability.

When the test pieces of this invention were used in test fluids such as, for example, urines containing occult blood, they exhibited stable performance of color formation.

According to the present invention, since the test piece is impregnated with at least one compound of the aforementioned general formula I in combination with an organic hydroperoxide, a chromogen and a buffer, the stability of the test piece to withstand degradation by aging is notably improved and the sensitivity of the test piece in the detection of occult blood in the body fluid is enhanced. The test piece, therefore, provides stable, accurate color formation on contact with the occult blood. It ensures sensitive and accurate detection of the occult blood.

What is claimed is:

1. In a test piece for the detection of occult blood or another peroxidatively active substance in body fluids including a substrate impregnated with an organic hydroperoxide, a chromogen, a buffer, and a stabilizer, the improvement wherein said stabilizer comprises at least one compound of the general formula I:

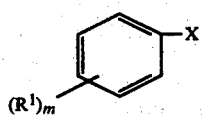

(I)

wherein, m denotes an integer of 1 to 5, $R^1$ denotes one member selected from the group consisting of methyl group, lower alkoxy group, halogen atoms and hydrogen atom, and X denotes one member selected from the group consisting of

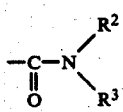

where, $R^2$ and $R^3$ each denote an alkyl group having 1 or 2 carbon atoms,

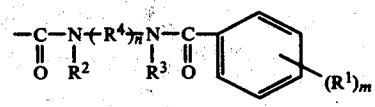

where, m, $R^1$, $R^2$, and $R^3$ are as defined above, $R^4$ denotes an alkylene group having 1 to 6 carbon atoms, and n is 0 or 1,

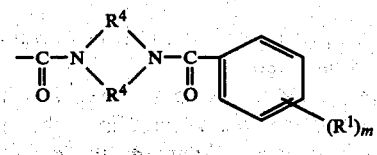

wherein, m, $R^1$, and $R^4$ are as defined above, and

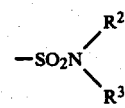

where, $R^2$ and $R^3$ are as defined above.

2. A test piece according to claim 1, wherein m denotes 1, $R^1$ denotes one member selected from the group consisting of methyl group, methoxy group, bromine atom, chlorine atom and hydrogen atom, and $R^4$ denotes an alkylene group having 2 to 6 carbon atoms respectively in the general formula I.

3. A test piece according to claim 1, wherein X denotes

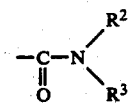

where, $R^2$ and $R^3$ are as defined above in the general formula I.

4. A test piece according to claim 1, wherein X denotes

where, m, $R^1$, $R^2$, $R^3$ and $R^4$ are as defined above in the general formula I.

5. A test piece according to claim 1, wherein X denotes

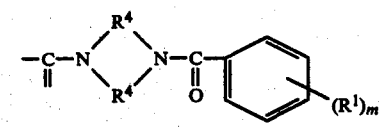

where, m, $R^1$, and $R^4$ are as defined above in the general formula I.

6. A test piece according to claim 1, wherein X denotes

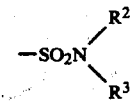

where, $R^2$ and $R^3$ are as defined above in the general formula I.

7. A test piece according to claim 1, which further comprises a wetting agent and a peroxidase activity enhancer.

8. A test piece according to claim 7, which further comprises a tackifier.

9. A test piece according to claim 2, wherein the stabilizer is a compound selected from the group consisting of p-bromobenzoyl dimethylamide, N,N'-dibenzoyl-N,N'-diethylethylene diamine, p-toluene sulfonyl-N-diethylamide, and N,N'-ditoluoyl-N,N'-diethylene diamine.

10. A test piece according to claim 9, wherein the organic hydroperoxide is at least one compound selected from the group consisting of 2,5-dimethylhexane-2,5-dihydroperoxide, cumene hydroperoxide, and 2,5-dimethylhexanone-2,5-dihydroperoxide.

11. A test piece according to claim 10, wherein the organic hydroperoxide is 2,5-dimethylhexane-2,5-dihydroperoxide.

12. A test piece according to any one of claims 9, 10 or 11, wherein said stabilizer is p-bromobenzoyl dimethylamide.

13. A test piece according to any one of claims 9, 10 or 11, wherein said stabilizer is N,N'-dibenzoyl-N,N'-diethylethylene diamine.

14. A test piece according to any one of claims 9, 10 or 11, wherein said stabilizer is p-toluene sulfonyl-N-diethylamide.

15. A test piece according to any one of claims 9, 10 or 11, wherein said stabilizer is N,N'-ditoluoyl-N,N'-diethylene diamine.

* * * * *